(12) United States Patent
Chua et al.

(10) Patent No.: US 10,188,475 B2
(45) Date of Patent: Jan. 29, 2019

(54) DRAPE FOR EQUIPMENT HAVING CYLINDRICAL OR OTHER NON-PLANAR CONTOURS

(75) Inventors: Mark Spencer G. Chua, Northbrook, IL (US); Peter S. Nichol, Grayslake, IL (US); Michael P. Layne, Needham, MA (US)

(73) Assignee: Medline Industries, Inc., Northfield, IL (US)

(*) Notice: Subject to any disclaimer, the term of this patent is extended or adjusted under 35 U.S.C. 154(b) by 2020 days.

(21) Appl. No.: 13/273,170

(22) Filed: Oct. 13, 2011

(65) Prior Publication Data
US 2013/0092177 A1    Apr. 18, 2013

(51) Int. Cl.
| A61B 46/00 | (2016.01) |
| A61B 46/10 | (2016.01) |
| A61B 6/00 | (2006.01) |
| A61B 5/055 | (2006.01) |
| G01R 33/28 | (2006.01) |

(52) U.S. Cl.
CPC ............ *A61B 46/10* (2016.02); *A61B 5/0555* (2013.01); *A61B 6/4423* (2013.01); *A61B 2562/247* (2013.01); *G01R 33/28* (2013.01)

(58) Field of Classification Search
CPC ..................... A61B 19/08; A61B 19/12; A61F 2013/15073
USPC .......................... 128/849, 853, 855
See application file for complete search history.

(56) References Cited

U.S. PATENT DOCUMENTS

| 3,025,957 A * | 3/1962 | Wall ........................ A61B 46/00 206/440 |
| 3,540,441 A | 11/1970 | Collins |
| 3,707,964 A | 1/1973 | Patience et al. |
| 3,835,851 A | 9/1974 | Villari |
| 3,881,476 A | 5/1975 | Bolker et al. |
| 3,952,738 A | 4/1976 | Krzewinski |
| 3,955,569 A | 5/1976 | Krzewinski et al. |
| 3,998,221 A | 12/1976 | Collins |

(Continued)

FOREIGN PATENT DOCUMENTS

WO   WO-2008/060364   5/2008

OTHER PUBLICATIONS

Medline Industries, Inc., "Drape, C-Arm, Mobile Xray", https://www.medline.com/b2b/load_catalog.do, Published prior to filing of the present application,(Unknown).

(Continued)

*Primary Examiner* — Ophelia A Hawthorne
*Assistant Examiner* — Caitlin Carreiro
(74) *Attorney, Agent, or Firm* — Philip H. Burrus, IV

(57) ABSTRACT

A drape (600) suitable for covering non-planar surfaces of equipment (1201) is provided. The drape (600) facilitates quick and efficient deployment while ensuring that a sterile field established by a drape portion (601) is not compromised. The drape (600) can include a drape wrapping layer (209) wrapped about a drape portion (601) that is formed initially with two abutting elongated accordion fold stacks (604,605). Non-sterile personnel (801) can handle the drape wrapping layer (209) to position the drape (600) along surfaces of the equipment (1201) without touching the sterile drape portion (601). Sterile personnel can then expand the abutting elongated accordion fold stacks (604, 605) to drape the surfaces of the equipment (1201).

16 Claims, 11 Drawing Sheets

(56) References Cited

U.S. PATENT DOCUMENTS

| | | | |
|---|---|---|---|
| 4,397,309 A * | 8/1983 | McAllester | A61B 46/00 128/855 |
| 4,627,427 A * | 12/1986 | Arco | A61B 46/00 128/853 |
| 5,197,493 A | 3/1993 | Grier-Idris | |
| 5,490,524 A | 2/1996 | Williams et al. | |
| 6,405,730 B2 | 6/2002 | Levitt et al. | |
| 6,497,233 B1 | 12/2002 | DeAngelis | |
| 2007/0175486 A1 | 8/2007 | Bogojevik et al. | |
| 2008/0006278 A1 | 1/2008 | Henke-Sarmento et al. | |
| 2011/0214679 A1 | 9/2011 | Chua | |

OTHER PUBLICATIONS

3M, INC., "Steri-Drape.TM C-Arm Drapes", http://solutions.3m.com/wps/portal/3M/en_US/IP/infectionprevention/solutions/sterile-field-surface/drapes/?PC_7_RJH9U5230GE3E02LECFTDQ0UD6_nid=GSSYGBPFYWbe88CZN1GGVJgl, Published prior to filing of the present application,(Unknown).

GE Healthacre, "C-Arm Drapes", http://www.gehealthcare.com/usen/xr/surdery/docs/SurgeryDrapes&Film.pdf, Published prior to filing of present application.,(Unknown).

Harris, Raymond E., "Non-Final Office Action", U.S. Appl. No. 12/717,704, filed Mar. 4, 2010; dated Jun. 21, 2012.

Harris, Raymond E., "Final Office Action", U.S. Appl. No. 12/717,704, filed Mar. 4, 2010; dated Oct. 2, 2012.

Harris, Raymond E., "Notice of Allowance", U.S. Appl. No. 12/717,704, filed Mar. 4, 2010; dated Feb. 20, 2013.

Choi, Seok K., "PCT Search Report", PCT/US2012/059492; Filed Oct. 10, 2012; dated Mar. 18, 2013.

\* cited by examiner

DRAPE FOR EQUIPMENT HAVING CYLINDRICAL OR OTHER NON-PLANAR CONTOURS

BACKGROUND

Technical Field

This invention relates generally to drapes, and more particularly to drapes for equipment having non-planar contours, such as Magnetic Resonance Imaging (MRI) and other medical equipment.

Background Art

In clinical environments, such as hospitals, medical offices, and ambulatory surgical centers, a wide range of equipment is used to perform diagnostics and procedures. This equipment can include devices like imaging equipment, ultrasound probes, microscopes, and radiographic equipment. This equipment is generally large.

At the same time, healthcare facilities are increasingly concerned about the occurrence of secondary complications occurring during medical and surgical procedures. For example, during a medical procedure on an otherwise healthy patient, there is the possibility that a secondary infection or other complication can result. As a result, more attention is being turned to establishment and maintenance of sterile fields about patients and procedure sites during medical procedures. For example, some healthcare facilities request medical professionals to check and double check certain conditions, such as whether a proper sterile field has been established or whether a proper sterile field can be maintained.

When a procedure involves a large piece of equipment, establishment and maintenance of sterile fields can become a complex problem. To begin, adequately cleaning and sterilizing the various surfaces and contours of the equipment between usages is difficult. This makes it challenging for medical professionals to ensure that patients are not inadvertently exposed to surgical fluids or other contaminants disposed on the equipment. Moreover, even where a sterile field is established, it is difficult to ensure that the sterile field is maintained. A single non-sterile person coming into contact with a previously sterilized surface can compromise a sterile field.

There is thus a need for an apparatus and method for easily establishing and maintaining a sterile field on equipment, even where the equipment has non-planar surfaces.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
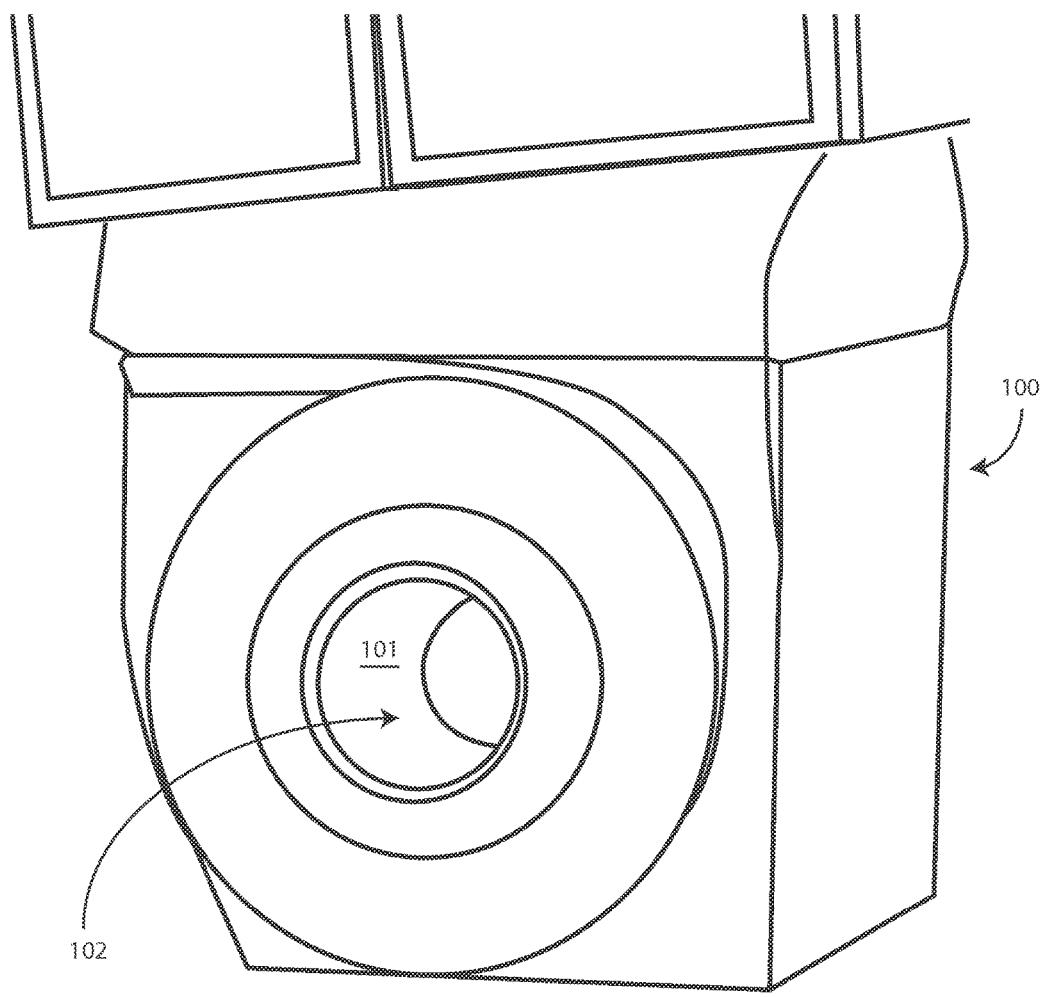
FIG. 1 illustrates a prior art medical device having non-planar usage surfaces.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide an equipment drape, suitable for use with medical or other equipment having non-planar surfaces, that is simpler to unfold and quicker to apply to non-standard surfaces than are prior art drapes. Moreover, embodiments of the present invention facilitate this simpler, quicker deployment without the risk of compromising sterile fields. The ease and efficiency with which embodiments of the present invention can be used is due in part to the way that embodiments of the present invention are folded. The ease and efficiency is also due to the constituent parts of each apparatus, some of which are handled by non-sterile personnel and some of which are handled by sterile personnel. Additionally, while some prior art drapes took six or more steps or mechanical manipulations, each of which had to be performed only by sterile personnel who risk contamination with every step, embodiments of the present invention can be put into use with far fewer steps, and with sterile personnel performing even fewer steps, thereby reducing the risk of compromising their sterile status.

While medical applications will be used herein for illustrative purposes and simplicity of discussion, it will be clear to those of ordinary skill in the art having the benefit of this disclosure that applications for embodiments of the present invention are not so limited. Embodiments of the present invention can be used in any application where non-planar surfaces need to be protectively covered on a relatively large piece of equipment.

FIG. 1 illustrates a piece of medical equipment 100 having non-linear surfaces 101. The explanatory piece of medical equipment 100 is a MRI machine, although embodiments of the invention are not limited either to MRI machines or medical machines, as noted in the preceding paragraph.

The MRI machine has a cylindrical patient port 102. This particular MRI machine is suspended from the ceiling in a medical facility. The MRI machine is moveable along two beams and can be transitioned from a non-sterile environment, such as a storage room, into a sterile environment, such as an operating machine. Accordingly, medical professionals are capable of imaging a patient undergoing surgery or other procedures without moving the patient to another room. If, for example, a patient is sedated and undergoing surgery, the medical professional is able to cause the MRI machine to enter the operating room so that the patient can be imaged.

As can be appreciated, it is imperative that sterile fields about the patient be maintained. For instance, if a patient has a surgical opening, contact with a non-sterile surface could potentially cause the patient to suffer from a secondary complication. Consequently, the cylindrical patient port 102 must be completely sterile. This can be accomplished in one of two ways. The first is to fully sterilize the MRI machine between each use. As noted above, cleaning can be a difficult process. The illustrative MRI machine of FIG. 1 is large, weighing approximately 17 tons. Ensuring that the entire cylindrical patient port 102 is completely sterile is difficult and incredibly time consuming.

The second method is to "drape" the cylindrical patient port 102. Draping involves covering the non-linear surfaces 101 to which the patient has access with a sterile covering. Prior art attempts include adhesively coupling flat, rectangular sheets in layers about the entire non-linear surface. This method has problems as well. First, sterile personnel must perform the draping procedure. If non-sterile personnel drape the cylindrical patient port 102, the sterility of the drape is compromised. However, since the MRI machine is not sterilized between procedures, non-patient surface 103 may not be sterile. If sterile personnel come in contact with such a non-patient surface 103, their sterile condition is compromised. Accordingly, they must re-perform the sterilization process, which is again time consuming.

Embodiments of the present invention solve this process by providing a drape that is wrapped within a drape wrapping layer. The drape wrapping layer, which can be handled by non-sterile personnel, can be unfolded to reveal a sterile drape portion. In one embodiment, the sterile drape portion is configured with accordion folds to form two abutting stacks. Sterile personnel can then expand the accordion folded stacks to drape non-planar surfaces of medical equipment. In one or more embodiments, coupling devices can be attached to the sterile drape portion to make attachment and detachment of the sterile drape portion to the medical equipment even simpler.

Figure 2:
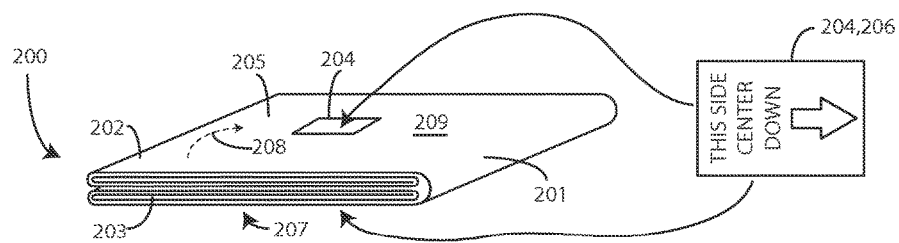
FIG. 2 illustrates a folded drape configured in accordance with one or more embodiments of the invention.

Turning to FIG. 2, illustrated therein is a folded drape 200. The folded drape 200 includes a book fold 201 disposed between two folded drape halves 202,203. The two folded drape halves 202,203 are arranged such that the major faces (301,302 of FIG. 3 below) of each folded drape half 202,203 are disposed adjacent with each other in a shared relationship. As a first step in a draping operation, the book fold 201 can be unfolded 208, which results in the semi-folded drape (300) shown in FIG. 3.

The exterior surfaces of the folded drape 200 that are visible in FIG. 2 are a drape wrapping layer 209. In one embodiment, the drape wrapping layer 209 is a Central Sterile Reprocessing (CSR) wrap that is used widely by medical professionals in hospitals, ambulatory surgical centers, and the like during medical procedures. While a CSR wrap is one example of a wrap that can be used, it will be clear to those of ordinary skill in the art that other wraps, such as plastic, cotton, linen, paper, or combinations thereof, can be substituted without departing from the spirit and scope of the invention. For example, the drape wrapping layer 209 can be manufactured from other materials, such as spunbond-meltblown-spunbond material. Other materials can be used for the drape wrapping layer 209, including, for example, various woven, non-woven, hydroentangled materials, and/or combinations thereof, absorbent Airlaid, spunlace, blends of polyester, polypropylene, polyethylene, urethane, and/or combinations thereof, using various methods, including a spunbond metblown spundbond (SMS) method, a spunbond metblown metblown spundbond method (SMMS), and a spunbond metblown metblown spundbond method (SMMMS). Suppliers of such materials include Cardinal Health in Dublin, Ohio, Kimberly Clark in Neena, Wis., Molnycke Health Care in Newtown, Pa., and Precept Medical Products, Inc., in Arden, N.C. One or more antimicrobial layers can be added to the drape wrapping layer 209 further enhance antimicrobial protection. Additionally, the drape wrapping layer 209 can optionally include and water resistant lining that prevents the passage of fluids through the material.

In one embodiment, the drape wrapping layer 209 is configured to be opaque. For example, in one embodiment, the drape wrapping layer 209 comprises a blue CSR wrap. As will be shown below with reference to FIG. 7, in one embodiment a drape portion is non-opaque, and can be translucent, transparent, or pellucid. In accordance with one or more methods described herein, non-sterile personnel can handle the drape wrapping layer 209, while sterile personnel handle the drape portion. By making the drape wrapping layer 209 opaque, and the drape portion non-opaque, the overall assembly provides a simple, clear mnemonic device to personnel regarding which portion is to be handled by sterile personnel and which is to be handled by non-sterile personnel.

The explanatory folded drape 200 of FIG. 2 includes one or more indicators 204,206 disposed on an outer surface 205 of the folded drape 200. In the illustrative embodiment of FIG. 2, two indicators 204,206 are included, with a first indicator 204 being disposed on an upper outer surface 205, and a second indicator 206 being disposed on a lower outer surface 207. The indicators of this explanatory embodiment provide indications of which portion of the folded drape 200 are configured to be the bottom portion when the folded drape 200 is ultimately unfolded. For instance, the indicators 204,206 of FIG. 2 read "this side center down" and include an arrow that indicates how to unfold the folded drape 200. Other indicators can be used, and will be readily obvious to those of ordinary skill in the art having the benefit of this disclosure. Using the indicators 204,206 of the explanatory embodiment of FIG. 2, medical personnel is instructed regarding which outer surfaces 205,207 of the folded drape 200 should be placed adjacent to the non-planar surfaces of the medical equipment.

Figure 3:
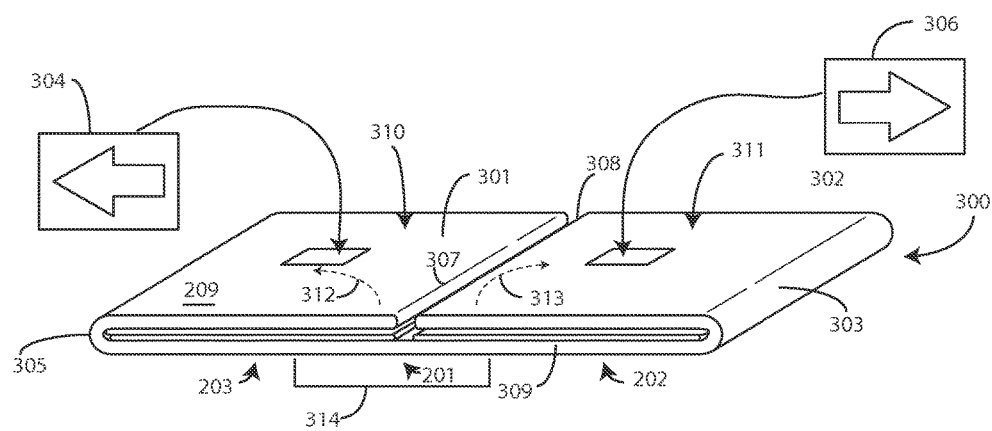
FIG. 3 illustrates a partially unfolded drape configured in accordance with one or more embodiments of the invention.

Turning to FIG. 3, illustrated therein is a semi-folded drape 300. The semi-folded drape 300 results from unfolding the book fold 201 between the two folded drape halves 202,203. Unfolding the book fold 201 also reveals the major faces 301,302 that were shared in the folded drape (200) of FIG. 2.

As shown in FIG. 3, two additional indicators 304,306 are revealed when the book fold 201 is unfolded. The indicators 304,306 are disposed along the drape wrapping layer 209. The indicators 304,306 of FIG. 3, which were hidden in FIG. 2, provide instruction to personnel regarding how to unfold the semi-folded drape 300 to obtain the partially folded drape (400) shown in FIG. 4. In this illustrative embodiment, the indicators 304,306 are arrows instructing personnel to open book folds 303,305. Symbols are useful on indicators 304,306 because they are universal and are not defined by a particular language. However, it will be clear to those of ordinary skill in the art having the benefit of this disclosure that text or other indicia can be placed on indicators 304,306 as well.

The semi-folded drape 300 includes two book folds 303,305. When the two book folds 303,305 are present, a first semi-folded drape end 307 passes over a base member 309, with a first semi-folded drape portion 310 sharing a major face with the base member 309. Similarly, a second semi-folded drape end 308 passes over the base member 309, with a second semi-folded drape portion 311 sharing a major face with the base member 309. As shown in FIG. 3, in one embodiment the first semi-folded drape end 307 abuts the second semi-folded drape end 308 along a central portion 314 of the semi-folded drape 300.

Figure 4:
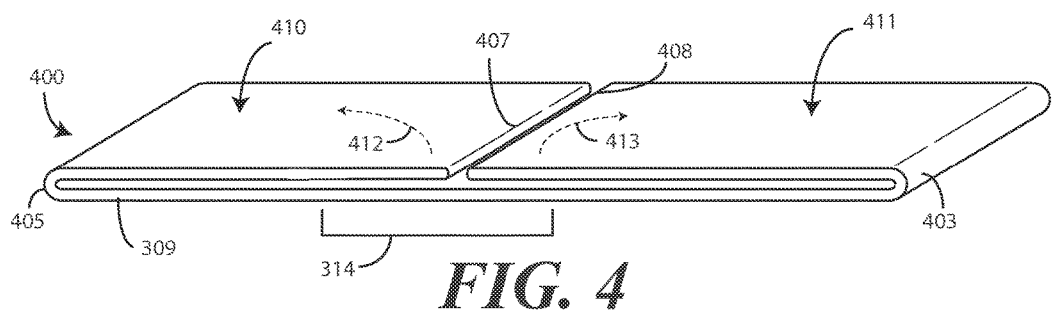
FIG. 4 illustrates a partially unfolded drape configured in accordance with one or more embodiments of the invention.

When personnel unfolds 312,313 the book folds 303,305 in accordance with the arrows present on the indicators 304,306, the result is the partially folded drape 400 shown in FIG. 4. Turning now to FIG. 4, the partially folded drape 400 includes two additional book folds 403,405.

The book folds 403,405 of FIG. 4 combine with the book folds (303,305) of FIG. 3 to form a "double book fold." The double book fold is useful in many applications. For example, where used with a MRI machine, the cylindrical patient port (102) can have a length of nearly six feet. One of the difficulties of draping such a cylindrical patient port (102) is that it is difficult for someone to pass something from one end to the other while preserving the sterile field. The double book fold allows a long component to be manageably placed in a pouch or shipping container, yet yields a long device sufficient to span the length of a cylindrical patient port.

When the two book folds 403,405 are present, a first partially folded drape end 407 passes over a base member 409, with a first partially folded drape portion 410 sharing a major face with the base member 309, which has become elongated compared with the semi-folded drape (300) of FIG. 3 due to the unfolding (312,313) of book folds (303, 305). Similarly, a second partially folded drape end 408 passes over the base member 309, with a second partially folded drape portion 411 sharing a major face with the base member 309. In one embodiment, the first partially folded drape end 407 abuts the second partially folded drape end 408 along a central portion 314 of the partially folded drape 400. When personnel unfolds 412,413 the book folds 403, 405, the result is the envelope folded drape 500 shown in FIG. 5.

Figure 5:
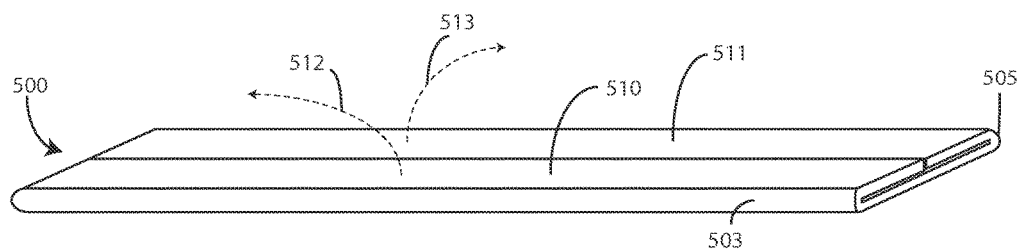
FIG. 5 illustrates a partially unfolded drape configured in accordance with one or more embodiments of the invention.

Turning to FIG. 5, a first envelope portion 510 and a second envelope portion 511 are wrapped about a drape portion with two book folds 503,405. The drape portion is not visible in FIG. 5, but will be visible when the first envelope portion 510 and the second envelope portion 511 are unfolded 512,513 about the two book folds 503,505. When this is done, the drape 600 of FIG. 6 results.

Figure 6:
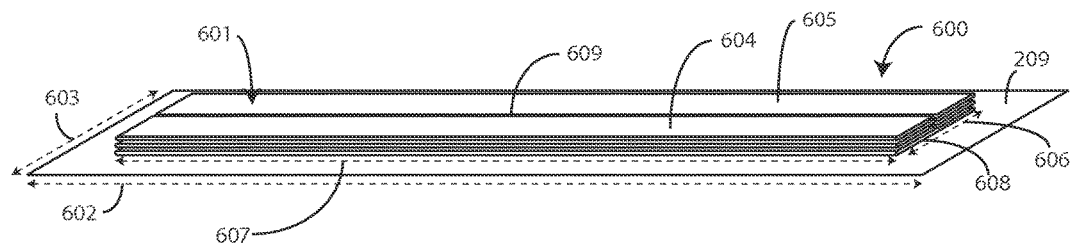
FIG. 6 illustrates a partially unfolded drape configured in accordance with one or more embodiments of the invention.

Turning now to FIG. 6, illustrated therein is a drape 600 configured to cover non-planar surfaces of equipment in accordance with one or more embodiments of the invention. The drape wrapping layer 209, having been unfolded as shown in FIGS. 2-4, is disposed beneath a drape portion 601. The drape wrapping layer 209 defines a wrapping layer length 602 and a wrapping layer width 603.

The drape portion 601 is disposed centrally along the drape wrapping layer 209. In this embodiment, the drape portion 601 is configured in two abutting elongated accordion fold stacks 604,605. A bottom section 608 spans and links the two abutting elongated accordion fold stacks 604,605. The two abutting elongated accordion fold stacks 604,605 each abut along a center-line 609. The two abutting elongated accordion fold stacks 604,605 of the drape portion 601 define a stack width 606 and a stack length 607. In the illustrative embodiment of FIG. 6, the stack width 606 is less than the wrapping layer width 603. Similarly, the stack length 607 is less than the wrapping layer length 602.

As noted above, in one embodiment, the drape portion 601 is configured to be translucent, transparent, or pellucid, while the drape wrapping layer 209 is configured to be opaque. In one embodiment, the drape portion 601 is manufactured from a clear 0.05 mm polyethylene sheet. However it will be clear to those of ordinary skill in the art having the benefit of this disclosure that other materials can be used as well. Such materials include blends of polyester, urethane, or other flexible materials. In one or more embodiments, the drape portion 601 is configured to be sterile.

Figure 7:
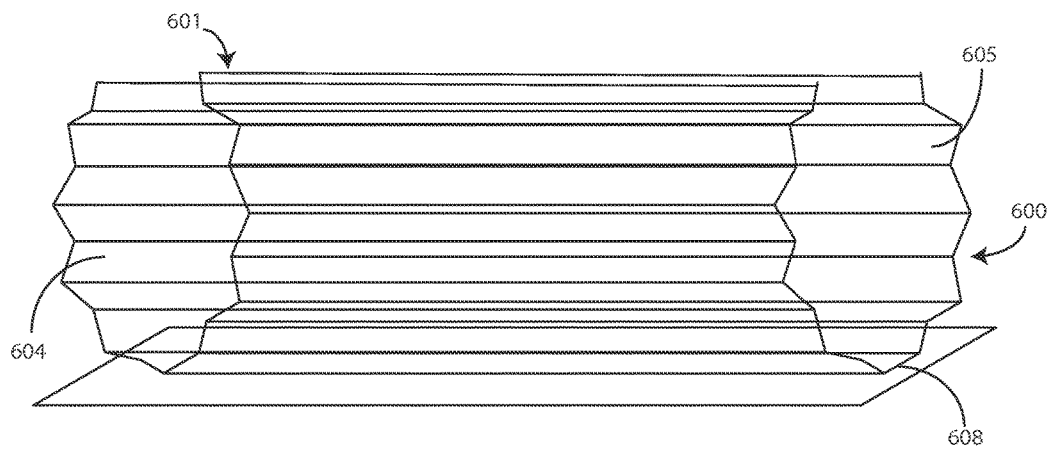
FIG. 7 illustrates a partially unfolded drape configured in accordance with one or more embodiments of the invention.

In practice, non-sterile personnel can perform the unfolding operations described in FIGS. 2-4. The non-sterile personnel are able to position, unfold, and move the drape by handling only the drape wrapping layer 209. Thus, the sterile drape portion 601 remains sterile. Once the non-sterile personnel position the drape 600 correctly, sterile personnel can then manipulate the drape portion 601 to expand the two abutting elongated accordion fold stacks 604,605 as shown in FIG. 7. Note that the bottom section 608 of the drape portion 601 can be more readily seen in FIG. 7. This sterile/non-sterile deployment process is shown in detail in FIGS. 8-10.

Figure 8:
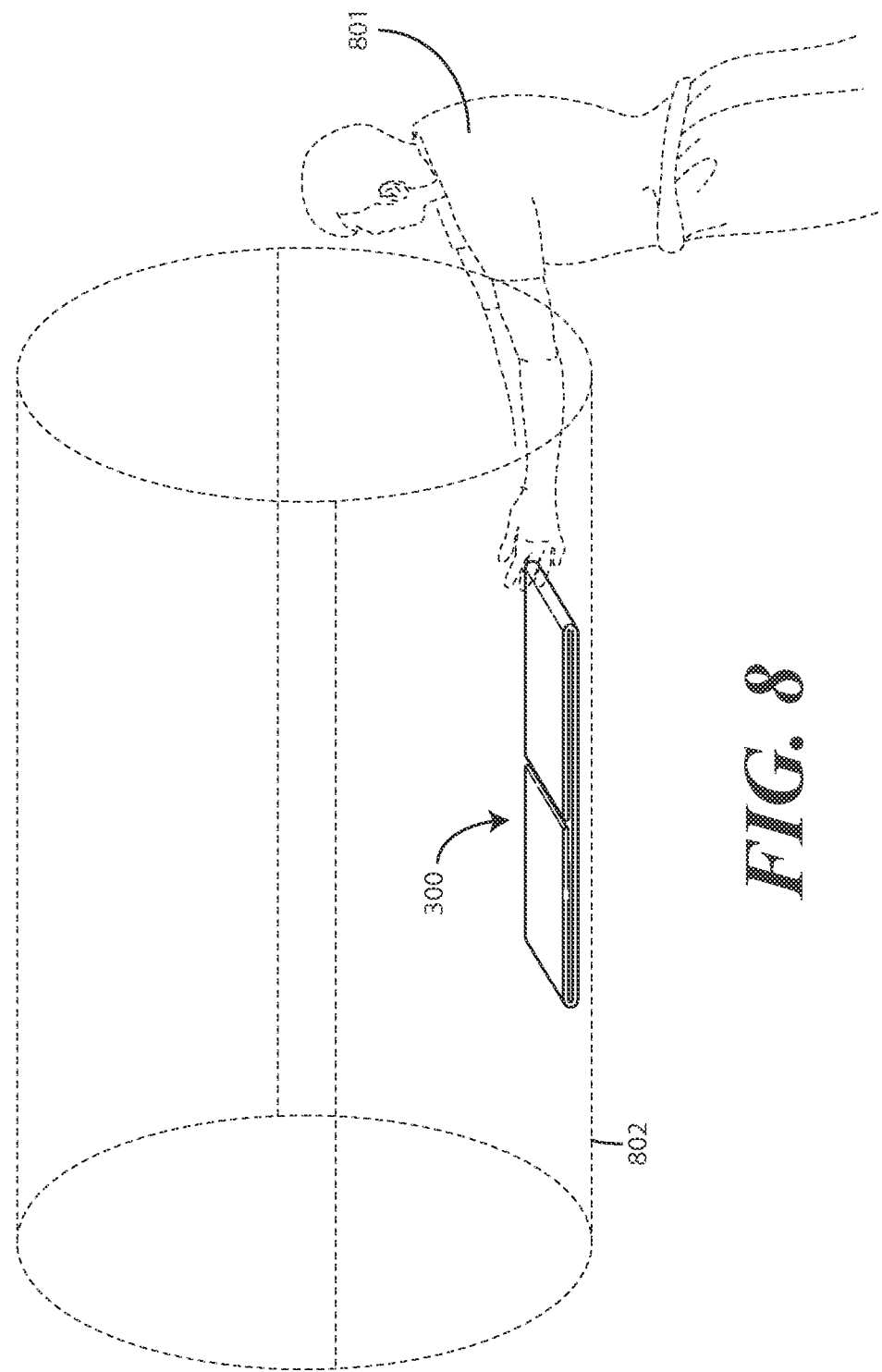
FIG. 8 illustrates a non-sterile worker initiating a draping operation in accordance with one or more embodiments of the invention.
Figure 9:
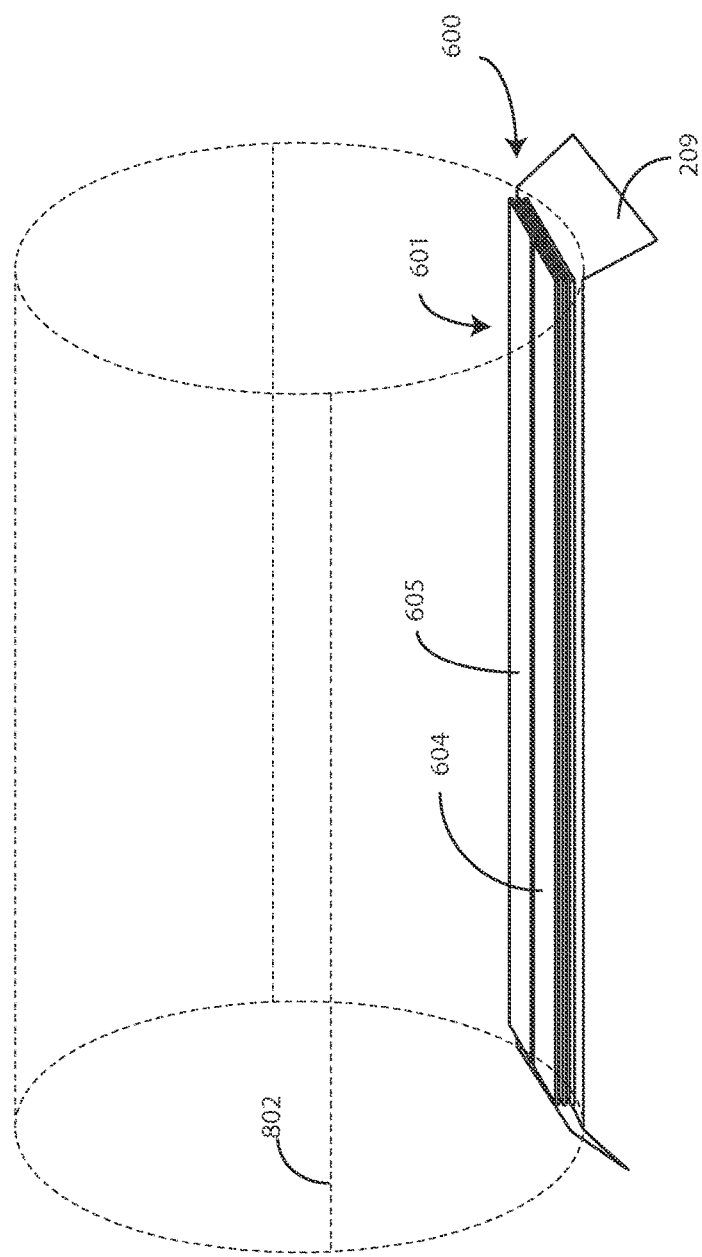
FIG. 9 illustrates completion of non-sterile operations in a draping operation configured in accordance with one or more embodiments of the invention.

Beginning at FIG. 8, non-sterile personnel 801 dispose the folded drape (200) of FIG. 2 along a surface 802 of equipment. In the illustrative embodiment of FIG. 8, the surface 802 is cylindrical, as would be the case if the equipment were a MRI machine such as the one shown in FIG. 1. In accordance with one or more indicators disposed on the folded drape (200), the non-sterile personnel 801 unfold the folded drape (200) to form the semi-folded drape 300 shown in FIG. 8. The non-sterile personnel 801 continues to unfold the semi-folded drape as described above with reference to FIGS. 3 and 4 to reveal the sterile drape portion 601 disposed atop the drape wrapping layer 209 as shown in FIG. 9. Handling only the drape wrapping layer 209, which covers a larger area than the two abutting elongated accordion fold stacks 604,605 of the drape portion 601, the non-sterile personnel (801) is able to position the drape 600 as necessary along the surface 802 of the equipment without compromising the sterile condition of the drape portion 601.

Figure 10:
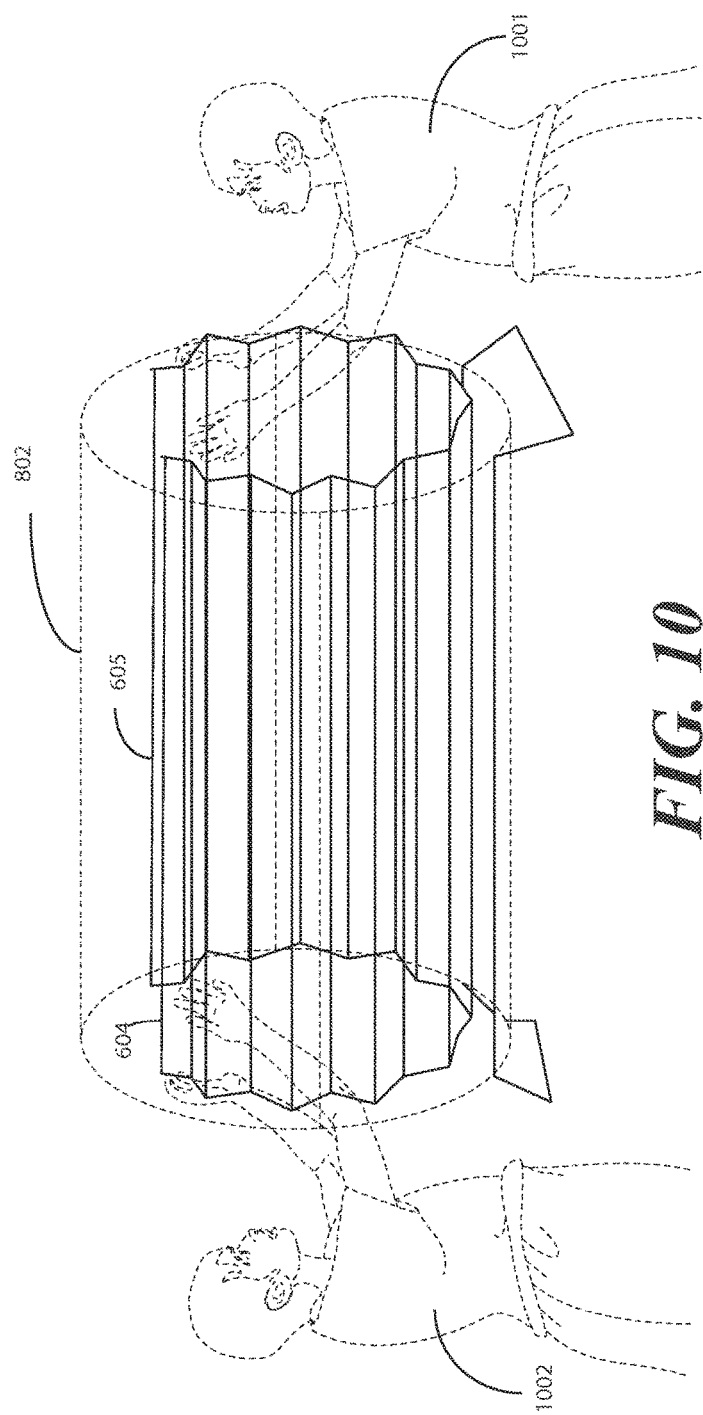
FIG. 10 illustrates sterile personnel performing one portion of a draping operation in accordance with one or more embodiments of the invention.

Turning to FIG. 10, once these steps are completed, sterile personnel 1001,1002 are then able to extend the two abutting elongated accordion fold stacks 604,605 along the surfaces 802 of the equipment. This process results in simple and efficient deployment of the drape portion 601 without compromising the sterile field defined by the drape portion 601.

Figure 11:
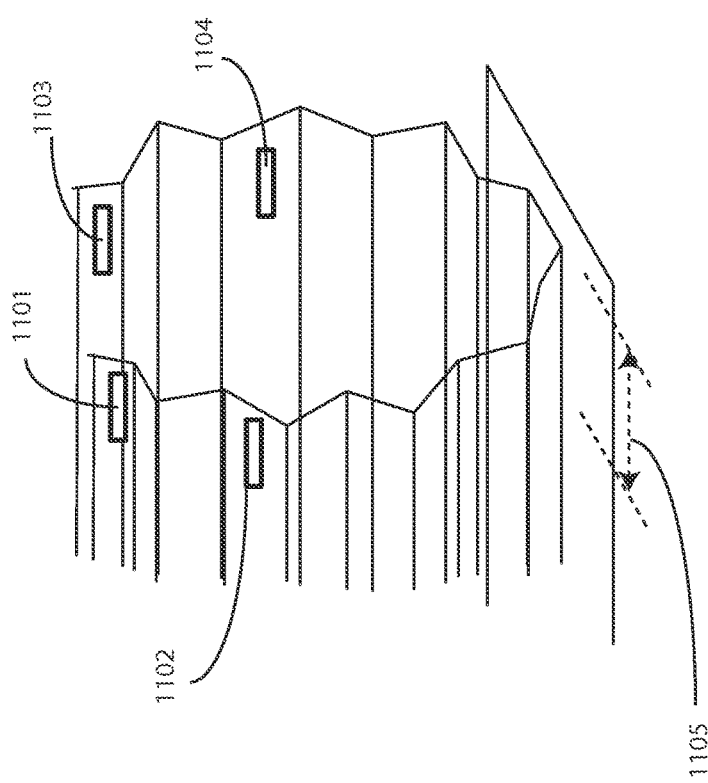
FIG. 11 illustrates a partially unfolded drape configured in accordance with one or more embodiments of the invention.

In one or more embodiments, to make attachment of the drape portion 601 to equipment easier, one or more coupling devices can be disposed both on the drape portion 601 and the equipment. Turning now to FIG. 11, one example of such coupling devices 1101,1102,1103,1104 is shown.

In the illustrative embodiment of FIG. 11, the coupling devices 1101,1102,1103,1104 are configured for selective attachment to the equipment. The coupling devices 1101, 1102,1103,1104 are disposed at distal ends of the drape portion 601. One such distal end 1105 is shown in FIG. 11. In one embodiment, the coupling devices 1101,1102,1103, 1104 comprise portions of hook and loop fasteners. A complementary portion of the hook and loop fastener can then be disposed on the equipment. For example, coupling devices 1101,1102,1103,1104 can be the "loop" portion of a hook and loop fastener, while the complementary portions disposed on the equipment are the "hook" portions. The opposite configuration can be used as well. While hook and loop fasteners are one type of coupling or attachment device suitable for use with the drape portion 601, it will be clear to those of ordinary skill in the art having the benefit of this disclosure that other coupling devices can be used as well. Examples include snaps, hooks, magnets, adhesives, and so forth. Thus, in one embodiment of a deployment process, after the sterile personnel (1001,1002) expand the two abutting elongated accordion fold stacks (604,605) as shown in FIG. 10, they may attach the drape portion 601 to the equipment 1201 as shown in FIG. 12.

Figure 12:
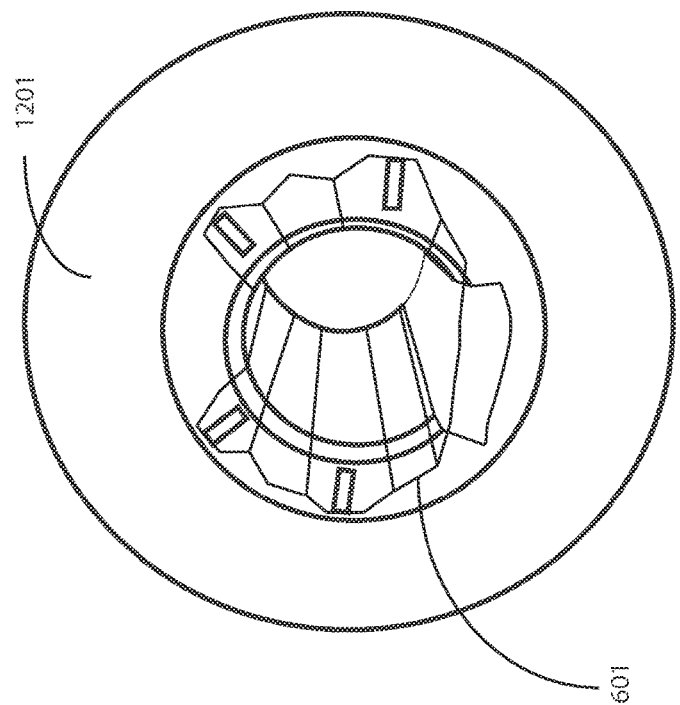
FIG. 12 illustrates an unfolded drape attached to a piece of equipment having non-planar usage surfaces in accordance with one or more embodiments of the invention.

While the drape portion 601 of FIG. 12 drapes the entirety of the cylindrical patient port, some applications will require only a portion of a non-planar surface to be draped. Recall from above that the equipment 100 of FIG. 1 was moveable along rails mounted to the ceiling into an operating room to scan a patient undergoing surgery. In such environments, the patient is likely laying on a sterile work surface. Where this is the case, it may be unnecessary to drape the bottom portion of the cylindrical patient port because the sterile field is provided by the work surface. Moreover, draping the bottom half of the cylindrical patient port may cause the work surface to snag on the drape portion 601 when the equipment 1201 passes about the work surface.

Figure 13:
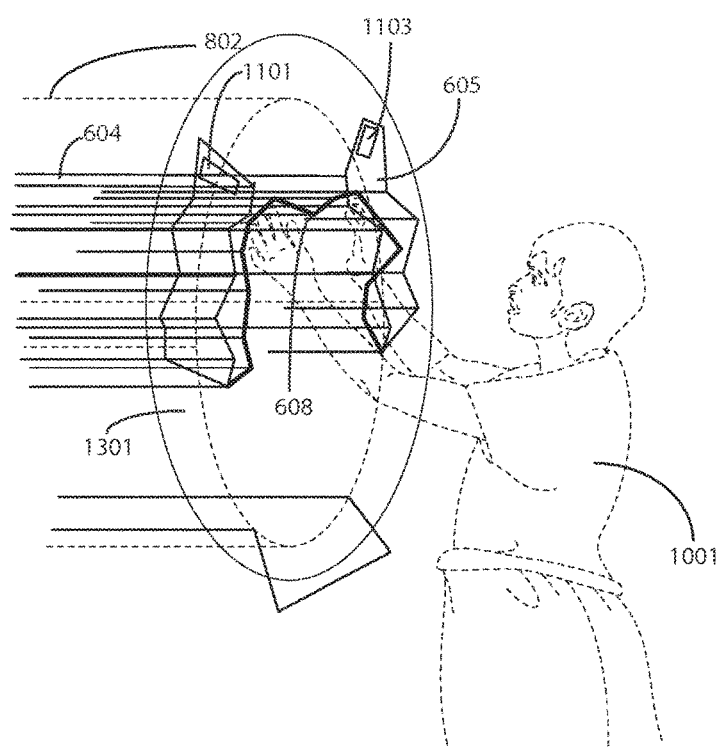
FIG. 13 illustrates sterile personnel performing one portion of a draping operation in accordance with one or more embodiments of the invention.

To accommodate such environments, an alternate method of attaching a drape portion 601 to equipment is shown in FIG. 13. FIG. 13 illustrates a next step that can occur after the step shown in FIG. 10, where sterile personnel 1001 (1002) extend the two abutting elongated accordion fold stacks 604,605 along the surfaces 802 of the equipment. As shown in FIG. 13, two coupling devices 1101,1103 are attached to an outer surface 1301 of the equipment. Once this is complete, the bottom section 608 can be lifted by the sterile personnel 1001 for attachment to only the top surfaces of the equipment. This process results in simple and efficient deployment of the drape portion 601 along only a portion of the surface 802.

Figure 14:
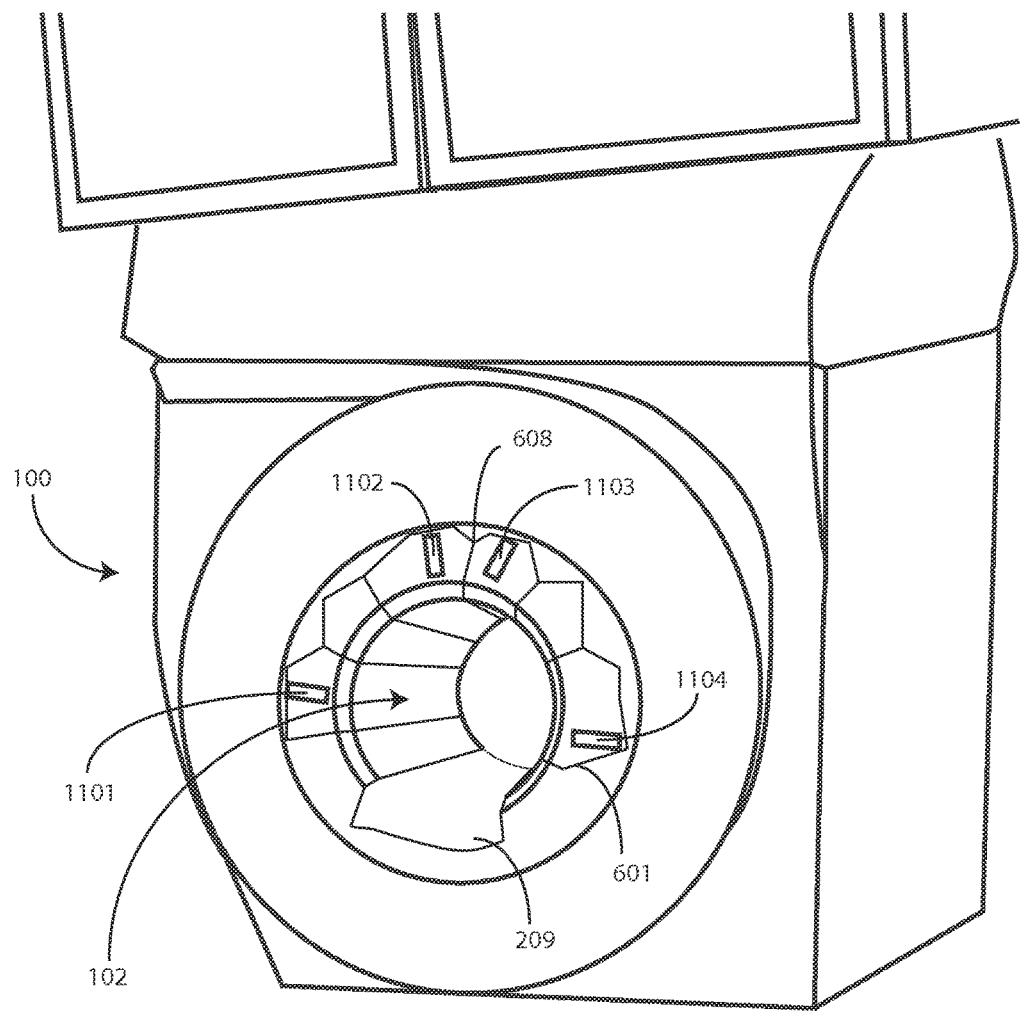
FIG. 14 illustrates one embodiment of a drape configured in accordance with one or more embodiments of the invention being attached to the medical device of claim 1.

Turning to FIG. 14, illustrated therein is the alternate embodiment of the drape portion 601 after having been deployed and attached to the medical equipment 100 of FIG. 1. In FIG. 14, the drape portion 601 is configured to only cover the upper portion of the cylindrical patient port 102. As noted, such an embodiment would be suitable for use in an operating room where a patient is lying on a sterile work surface. The sterile work surface could be passed through the cylindrical patient port 102. To ensure the sterile work surface is not compromised, the upper surface of the cylindrical patient port 102 is covered by the drape portion 601. Since the sterile work surface covers the lower portion of the cylindrical patient port 102, it may not be necessary to drape that portion as well.

FIG. 14 is the result of a deployment process shown in FIG. 13 in which non-sterile personnel (801) disposed a folded drape (200) along a surface of the equipment 100. In this illustration, the surface is the cylindrical patient port 102 of the MRI machine. The non-sterile personnel (801) then unfolded the folded drape (200) to reveal the sterile drape portion 601, which was initially configured as two abutting elongated accordion fold stacks (604,605) linked by a bottom section 608 and disposed centrally along a drape wrapping layer 209 (which is still present in FIG. 14, but would be removed prior to a patient being passed through the cylindrical patient port 102). Sterile personnel then extended the two abutting elongated accordion fold stacks (604,605) of the drape portion 601 along surfaces of the equipment 100, and attached the sterile drape portion to the equipment 100 using coupling devices 1101,1102,1103,1104 to define a sterile area along an upper portion of the cylindrical patient port 102.

Figure 15:
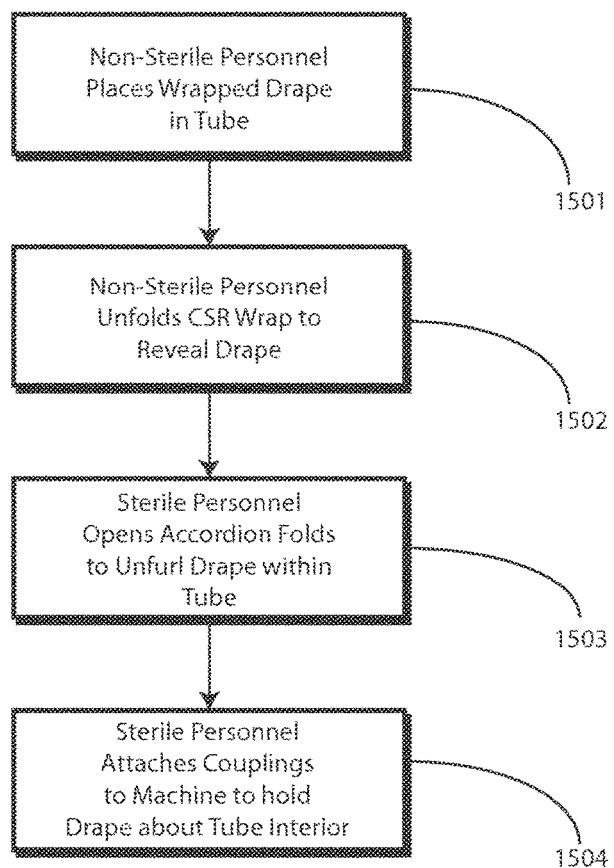
FIG. 15 illustrates a method of using a drape configured in accordance with one or more embodiments of the invention.

Turning to FIG. 15, illustrated therein is a flow chart showing the method described pictorially above for deploying a drape configured in accordance with embodiments of the invention. At step 1501, a folded drape is disposed along a surface of equipment. In one embodiment, non-sterile personnel perform step 1501.

At step 1502, the folded drape is unfolded to reveal a sterile drape portion comprising a bottom section linking two abutting elongated accordion fold stacks. Where indicators on the folded drape are provided, step 1502 can include reading one or more indicators prior to the disposing to determine how to dispose the folded drape along the surface of the equipment.

At step 1503, the two abutting elongated accordion fold stacks are extended along surfaces of the equipment. In one embodiment, sterile personnel perform step 1503. At step 1504, the sterile drape portion is attached to the equipment. In one embodiment, step 1504 is accomplished by using attachment devices that are disposed on distal ends of the sterile drape portion. For example, step 1504 can include fastening a first portion of a hook and loop fastener disposed on the sterile drape portion to another portion of the hook and loop fastener disposed on the equipment.

Figure 16:
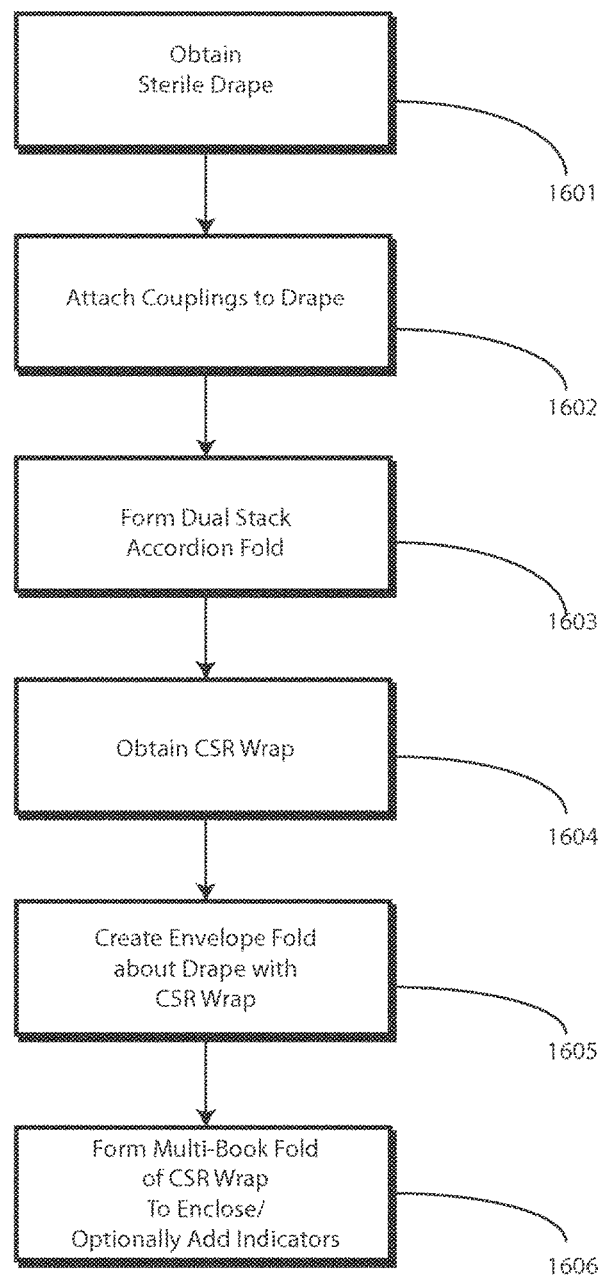
FIG. 16 illustrates a method of manufacturing a drape in accordance with one or more embodiments of the invention.

Turning now to FIG. 16, illustrated therein is one explanatory method of making a drape configured in accordance with one or more embodiments of the invention. At step 1601, a sterile drape portion is obtained. This can be accomplished by manufacturing the drape and sterilizing it, or by sourcing a drape layer and sterilizing it. At optional step 1602, one or more coupling devices can be attached to the sterile drape portion. In one embodiment, the coupling devices are attached to the drape portion at distal ends. Such an embodiment is useful for draping operations used for MRI machines with cylindrical patient openings. At step 1603, the sterile drape is configured with accordion folds to form two abutting elongated accordion fold stacks linked by a bottom section.

At step 1604, a drape wrapping layer is obtained. In one embodiment, the drape wrapping layer is a CSR wrap. At step 1605, the sterile drape portion is wrapped with the drape wrapping layer to form a wrapped drape. This step 1605 can include by creating an envelope fold with the drape wrapping layer about the drape portion. At step 1606, one or more book folds are created to form a folded drape. One or more indicators can be attached to the drape wrapping layer in either step 1605 or step 1606. For example, the indicators can provide instruction in how to unfold the drape wrapping layer. Alternatively, the indicators can indicate which portion of a folded drape wrapping layer is configured as a bottom portion of the folded drape wrapping layer when unfolded.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A method of manufacturing a drape, comprising:
   configuring a sterile drape with accordion folds to form two abutting elongated accordion fold stacks linked by a bottom section;
   wrapping the sterile drape with a drape wrapping layer to form a wrapped drape; and
   folding the wrapped drape with one or more book folds to form a folded drape.

2. The method of claim 1, further comprising attaching coupling devices to the sterile drape prior to the wrapping.

3. The method of claim 2, further comprising attaching one or more indicators to the drape wrapping layer.

4. The method of claim 1, the drape wrapping layer having a wrapping layer length and a wrapping layer width, the two abutting elongated accordion fold stacks defining a stack width and a stack length, the stack width is less than the wrapping layer width and the stack length is less than the wrapping layer length.

5. The method of claim 1, the sterile drape pellucid and the drape wrapping layer opaque.

6. The method of claim 1, the sterile drape polyethylene.

7. The method of claim 1, the drape wrapping layer a Central Sterile Reprocessing (CSR) wrap.

8. The method of claim 1, the configuring comprising coupling attachment devices to distal ends of the sterile drape.

9. The method of claim 8, the attachment devices comprising portions of hook and loop fasteners.

10. The method of claim 1, the configuring comprising configuring indicators to provide instructions in how to fold and unfold the sterile drape.

11. The method of claim 1, the configuring comprising configuring indicators to indicate which portion of the drape wrapping layer is a bottom portion when unfolded.

12. The method of claim 1, the drape wrapping layer comprising a first envelope portion and a second envelope portion, the first envelope portion being wrapped about one of the two abutting elongated accordion fold stacks and the second envelope portion being wrapped about another of the two abutting elongated accordion fold stacks to form an envelope folded drape.

13. The method of claim 12, the envelope folded drape comprising a first book fold and a second book fold, the first book fold and the second book fold resulting in a first envelope folded drape end and a second envelope folded drape end abutting along a central portion of the envelope folded drape to form a partially folded drape.

14. The method of claim 13, the partially folded drape comprising a third book fold and a fourth book fold resulting in a first partially folded drape end and a second partially folded drape end abutting to form a semi-folded drape.

15. The method of claim 14, the semi-folded drape comprising a fifth book fold resulting in a first half of the semi-folded drape sharing a major face with a second half of the semi-folded drape to form the folded drape.

16. The method of claim 15, the folded drape with one or more indicators indicating which portion of the folded drape is configured as a bottom portion disposed on an outer surface of the folded drape.

* * * * *